United States Patent [19]

Pope et al.

[11] Patent Number: 4,723,958
[45] Date of Patent: Feb. 9, 1988

[54] PULSATILE DRUG DELIVERY SYSTEM

[75] Inventors: David G. Pope, Branchburg; Alan E. Royce, Somerset, both of N.J.

[73] Assignee: Merck & Co., Inc., Rahway, N.J.

[21] Appl. No.: 866,415

[22] Filed: May 23, 1986

[51] Int. Cl.[4] .............................................. A61K 9/22
[52] U.S. Cl. ............................. 604/890.1; 604/891.1; 604/892.1; 424/438; 514/30
[58] Field of Search ................................ 604/890–893, 604/93, 131, 140; 424/422, 423, 438

[56] References Cited

U.S. PATENT DOCUMENTS

| | | | |
|---|---|---|---|
| 3,656,483 | 4/1972 | Rudel | 604/892 |
| 3,732,865 | 5/1973 | Higuchi et al. | 604/892 |
| 3,760,804 | 9/1973 | Higuchi et al. | 604/892 |
| 3,760,806 | 9/1973 | Leeper | 604/892 |
| 3,995,632 | 12/1976 | Nakano et al. | 604/892 |
| 4,327,725 | 5/1982 | Cortese et al. | 604/893 |
| 4,381,780 | 5/1983 | Holloway | 425/438 |
| 4,595,583 | 1/1986 | Eckenhoff et al. | 604/892 |
| 4,623,330 | 11/1986 | Laby et al. | 604/131 |
| 4,642,230 | 2/1987 | Whitehead et al. | 604/892 |
| 4,671,789 | 6/1987 | Laby | 604/59 |

FOREIGN PATENT DOCUMENTS 132102  1/1985  European Pat. Off. .

OTHER PUBLICATIONS

ALZA Bulletin, "Using the ALZET Osmotic Pump to Generate a Circadian Rhythm", Bulleting 9166-1, ALZA Corporation (1981).

Primary Examiner—Dalton L. Truluck
Assistant Examiner—Denise Whelton
Attorney, Agent, or Firm—David L. Rose; Michael C. Sudol, Jr.

[57] ABSTRACT

There is provided a novel drug delivery system which provides for intermittent drug delivery with readily adjustable intervals between drug delivery pulses. This is accomplished by providing a multilayer device in which layers of active drug are readily expandable or erodable when contacted with the environment in which the drug is to be administered. The drug layer is alternated with an inert layer and a multiplicity of such layers are contained within a tube impervious to such environment but provided with an opening into such environment. The multiplicity of such layers is driven along the length of such tube towards the opening. The interval between pulses is determined by the rate the layers are driven along the tube and the sizes of the layers. The duration of the pulse is determined by the rate of expansion or dispersion of the active layer into the environment, wherein the rate of expansion or dispersion is greater than the rate the layers are driven along the tube.

20 Claims, 5 Drawing Figures

PULSATILE DRUG DELIVERY SYSTEM

BACKGROUND OF THE INVENTION

It is commonly encountered in medicine, in particular veterinary medicine, that the dosage of a particular drug, medicament or nutritional agent is not required on a daily basis, but should be given at intervals which may range from very few days to several weeks. Current therapy provides for the human patient to note or remember when a particular dose is due, and for a non-human patient to be located, brought to a central area and given the drug, all of which can lead to missed or mistimed dosing which is to the detriment of the patient. In veterinary medicine a pulsed delivery system is available which provides for non-drug containing sections alternated with active sections, all driven at a constant rate, with the interval between doses being determined by the size of the layer without drug; a larger non-drug layer will cause larger intervals. However, this leads to very large devices, suitable only for the largest animals, or a limitation on the number of doses that can be provided from a single device. Alternatively, convoluted devices, such as spirals can be prepared which will avoid an extremely long device, but will provide for considerably expanded girth. The instant invention provides for a pulsatile device of compact size which avoids all of the problems of the prior art devices.

SUMMARY OF THE INVENTION

This invention is concerned with a device of compact size which is capable of providing for the pulsed delivery of a drug, medicament or nutrient where the interval between pulses of the drug can be prolonged and accurately regulated. This is accomplished by providing a tube containing a multiplicity of layers with an opening for the drug and a constant driving force to expel the drug from the tube, with the drug layers being expandable or dispersable when they are exposed to the environment at the opening in order to provide the pulse and with the duration between the pulses being provided by inert, non-erodable, layers, wherein the rate of expansion or dispersion of the drug layer is greater than the constant driving rate. Thus, it is an object of this invention to describe such devices. It is a further object to describe the particular materials which provide the device with its pulsatile characteristics. A further device is to describe the mechanism for the expansion or dispersion of the active layers and for the constant driving force. A still further object is to describe the active drugs which are suitable for this device. Further objects will become apparent from a reading of the following description.

DESCRIPTION OF THE INVENTION

In its broadest aspects, this invention encompasses a device for administering multiple doses of a medicament into the physiological fluids of a patient, or the environmental fluids of an apparatus, over a prolonged period of time wherein no drug is administered in the intervals between the doses of the medicament. This is accomplished by providing for a constant driving force operating against a multiplicity of layers contained within an impervious compartment with an opening in the compartment remote from the constant driving force. The layers provide for a drug layer adjacent to an expansion layer, which may be combined into a single layer, and with inert and impervious spacer layers alternating with the adjacent drug layer and expansion layer or combined single drug/expansion layer.

In the operation of the pulsatile drug delivery device the constant driving force pushes the multiplicity of layers towards the opening at the opposite end of the layer compartment and the rate of dispersion or expansion of the medicament layer is greater than the constant driving force. As a medicament layer and its adjacent expansion/dispersion layer reach the opening, the physiological fluid causes the expansion or dispersion of the expansion layer which forces the medicament out of the opening. When the drug is fully expelled, the physiological fluid is then in contact only with the next inert spacer layer which does not erode and does not release any medicament into the physiological fluid. When the constant driving force has expelled the spacer layer, the next medicament layer and its adjacent expansion layer are then exposed to the physiological fluid and provide for a rapid pulse of medicament delivery. The duration between pulses can be readily controlled by varying the rate of the constant driving force and the thickness of the spacer layers as well as the thickness of the expansion, drug or combined drug/expansion layers. the duration of the pulse can be readily controlled by varying the characteristics of the expansion layer, or combined drug/expansion layer, or by varying the size of the opening. A thicker spacer layer will certainly cause a longer duration between pulses of drug since it will take a longer period of time for the thicker spacer layer to completely traverse the opening. Also however, thicker layers of drug, or a thicker expansion layer will also cause a longer duration between pulses since after the active and expansion layers have dispersed into the environment, a void will be left between the opening and the next spacer layer. The length of this void will have to be traversed by the next spacer layer, in addition to the length of the spacer layer itself, before the next drug pulse will begin. In addition, the duration of the pulse itself can be varied by adjusting the dispersion characteristics of the drug layer to provide for a longer or shorter duration of the pulse. Thus, it is apparent that the physical dimensions of the various layers, the dissolution or dispersion characteristics of the expansion and drug layers, the physical characteristics of the container, and the rate characteristics of the driving force can be readily varied to provide for a pulsatile drug delivery device with rate characteristics to match any situation desired. It should be further noted that the various layers need not be uniform in size. That is, the sizes of the expansion, drug or spacer layers can be adjusted to provide for a large initial dose followed by a series of smaller uniform doses; or the various layers could be planned to provide for a large initial dose followed by a series of doses of slowly decreasing or increasing size. The various doses could also be adjusted to correspond to seasonal needs of the animal administered the device or to provide for increasing doses to yield the correct constant dose rate for an animal which is increasing in size. The doses could also provide for a period of increased or decreased doses depending upon seasonal variations of parasite burdens or nutritional needs. The various layers can be further modified to provide for pulses of drug administration where different materials are administered in each pulse or in selected pulses. Such arrangements can thus accomplish in a single device various treatment regimens which are now accomplished by the multiple administration of individual dosages, thus resulting in considerable cost and manpower savings by removing the need to assemble and individually dose the animals as well as avoiding the stress put to the animal during such procedures.

The pulsatile drug delivery system can find utility in those situations where the delivery device remains in the physiological fluid for extended periods of time and is not removed by normal bodily processes such as by alimentary function. Thus, the pulsatile device is ideally suited for use in veterinary medicine as an oral delivery device in ruminants and in human or veterinary medicine as an implanted device such as a subcutaneous implant.

When used in ruminant animals, the pulsatile delivery device is constantly bathed in the fermenting aqueous ruminal contents and can ideally be used to provide pulses of medicaments or other materials for a prolonged period of time. To prevent the regurgitation and expelling of the device, it is advisable to provide a densifying agent to maintain the device at the bottom of the ruman or to provide the device with variable geometry to prevent its expulsion.

When used as a parenterally implanted device, the device will likewise be constantly contacted with physiological fluids and is thus suitable for the prolonged administration of medicaments or other materials. Parenteral implantation is generally carried out subcutaneously.

The materials which may be used as the physilogically active agent in this device can be any medicament for treating or preventing disease or nutrients to supplement the diet of the subject administered the device. Typical oral medications used in veterinary medicine would be antiparasitic agents, antibiotics, antiinflammatory agents, growth promotant and growth permittant agents, antifungal agents, corticosteroids and the like. A preferred medicament is a broad spectrum antiparasitic agent such as ivermectin. It is also often desirable to provide the animal with supplemental nutrient materials such as vitamins, minerals, amino acids and the like, and such nutrient materials are readily supplemented into the animals diet over a prolonged period of time.

Similarly, when used as an implanted device, the pulsatile drug delivery system can be used in human and veterinary medicine for the prolonged pulsatile delivery of antiparasitic agents, antibiotics, growth promotant and growth permittant agents, anticonvulsive agents, cardiovascular agents, corticosteroids, diuretics, hormones, enzymes, tranquilizers and the like.

Additional uses for the instant devices are possible. It is contemplated that the instant device may be usable in an animal metering trough to provide for a medicated water supply which avoids repetitive additions of medicaments to the trough. Also, the instant device is usable in agricultural areas, such as by placement in an irrigation system, to provide for the pulsed administration of materials usable by the agricultural crops such as soil nematocides, antifungal agents, and the like.

It will be appreciated by those skilled in the art that a further use of this device can be found in the industrial areas. There are many occasions where materials must be added to industrial water systems such as cooling towers and other circulating water systems to control algae and other microbial growth, pH and the like. By varying the size and contents of the instant pulsatile device, a system is readily contemplated whereby a compact cylindrical object could be place in the bottom of a circulating water system which could periodically inject the appropriate microbicide into the water system to avoid the periodic manual administration of such materials.

The instant invention is further described and explained by the attached drawings.

Figure 1:
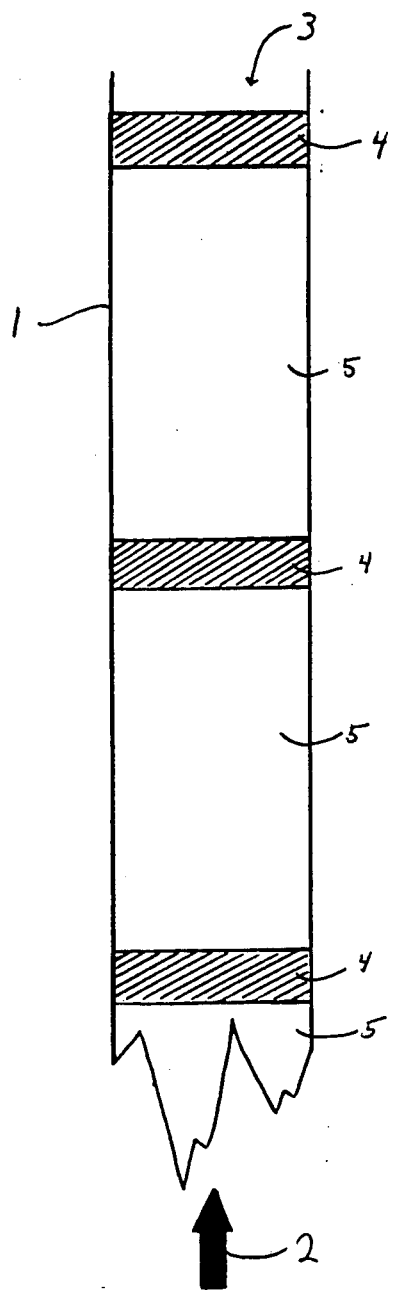
FIG. 1 is a drawing in cross-section of a typical prior art pulsatile delivery device.

Making specific reference to FIG. 1, a traditional pulsatile delivery device 1, is a container for the various layers contained within, where 2 is the constant driving force which pulses all of the layers towards the opposite, open end 3 of the container. The active layer 4 containing the medicament or nutrient material is alternated with an inert or placebo layer 5. Because the driving force is constant, the placebo layer can cause an increase in the interval between pulses only by increasing in physical size. This necessarily results in a device with at least one exceedingly large dimension, only a portion of which is shown in FIG. 1.

Figure 2:
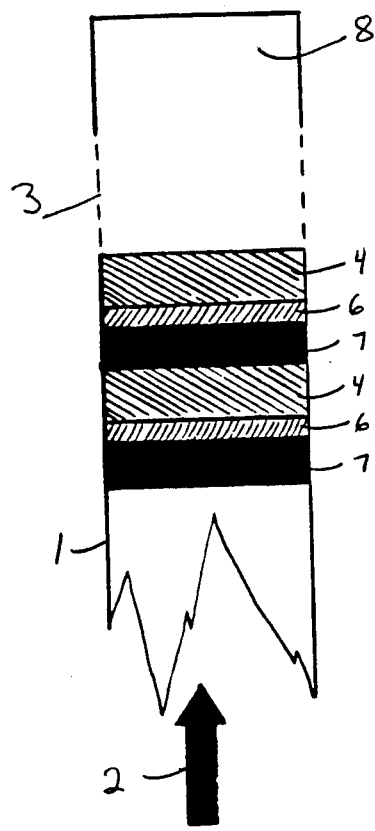
FIG. 2 is a drawing in cross-section of one version of the pulsatile delivery device of this invention with separate medicament and expansion layers.
Figure 4:
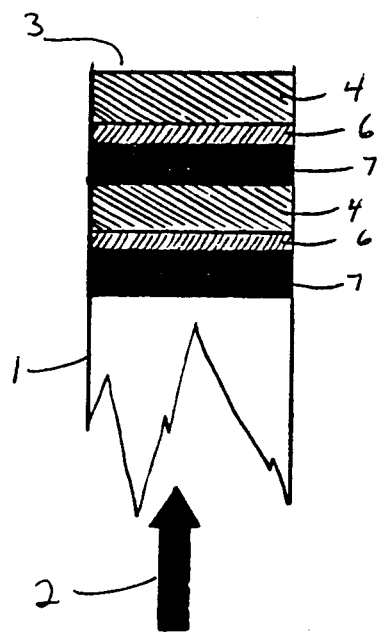
FIGS. 4 and 5 are drawings in cross-section of further embodiments of this invention.

In FIG. 2, a device of the instant invention, a container 1 with a constant driving force 2 at one end and an open end or an opening 3 at the opposite end causes the contents of the container to be driven towards the open end. The container is filled with layers of active material 4 followed by an expanding layer 6 and inert spacer layers 7, and continuing in that sequence. The opening 3 may be the entire cross-section of the container, as shown in FIG. 4, or preferably the opening 3 may be circumferential in the form of holes or slots. Additionally, an end of container 1 may be provided with a storage area 8 for the inert spacer layers 7 as they are pushed along the device. This arrangement prevents the inert spacer layers 7 from entering the physiological area being treated. This is particularly important when the instant device is used as a subcutaneous implant.

Figure 3:
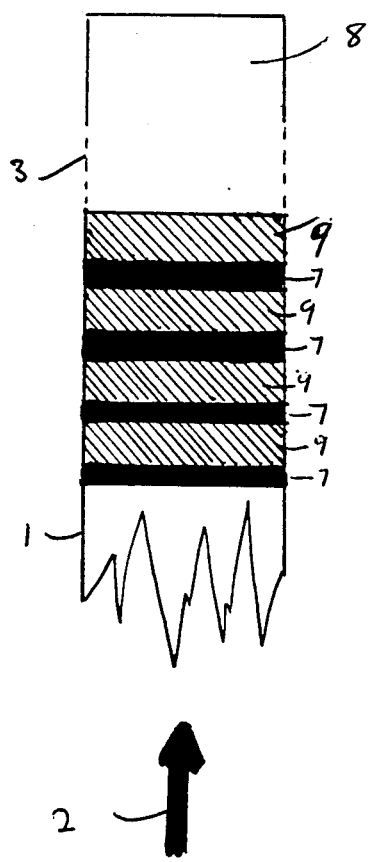
FIG. 3 is a drawing in cross-section of another version of the pulsatile delivery device of this invention with a combined medicament/expansion layer.

In FIG. 3, another version of the device of this invention is shown which is similar to that shown in FIG. 2 except that the separate medicament layer 4 and the expanding layer 6 have been combined into a single layer 9 containing both the medicament and the expanding agent. This layer alternates with the inert spacer layers 7 to function in the same manner as the device in FIG. 2.

In FIG. 4, as mentioned above, the storage area 8 of the container 3 has been dispensed with such that the expelled spacer layers 7 are allowed to enter the physiological area being treated. This type of device is particularly useful for the oral treatment of ruminant animals where the relatively small spacer layers 7 would not be any cause for concern.

The various elements of the instant pulsatile drug delivery system have preferred properties which will enable the device to be optimized to the particular conditions of use.

The container 1, is elongated with the constant driving force at one end and the opening at the opposite end. The container may be of any cross-sectional shape although a circular cross-section is generally preferred for oral administration. It may be preferred to use an oval cross-section when the device is to be used as a subcutaneous implant. The container 1 material may be any rigid or semi-rigid material including metal, glass or plastic material which is impermeable to water. Preferred plastic materials are thermoplastics such as polyethylene, polycarbonate, polypropylene and the like. It may be desirable to coat the outside of the container to improve the biocompatibility of the device and avoid unwanted physiological reactions. Preferred coating materials would be cellulosics and silicone elastomers. The coating may also be treated, such as with a heparinized coating to further reduce physiological reactions, particularly when the device is used as a subcutaneous implant. The inside surface of the container should be smooth to permit the unimpeded sliding of the column of layers along such inside surface. In addition, a lubricant may be added to facilitate the movement of the layers along the length of the container as well as to assist in the formation of a water-tight seal about the layers where they contact the inside surface. In particular, the spacer layers could be impregnated with a lubricant in order to facilitate movement and to prevent the premature incursion of water into the drug or expanding layers.

The constant driving force may be provided by any mechanism which is capable of producing small rates of travel of the layers over prolonged periods of time. The mechanism may be mechanical, electro-mechanical, chemical, or physico-chemical such as osmotic expansion which is the preferred means of driving the column of layers. The constant driving force may be separate from the container or it may be an integral part thereof. If the constant driving force is separate from the container, it would be attached to the container prior to use. Typically, the constant driving force is in a dormant state until it is placed in the physiological or environmental area of use. In the case of an osmotic pump as the constant driving force, the driving force will not start until the device is placed in an aqueous medium whereupon the osmotic action will start expanding a fluid against the column of layers, pushing them towards the opening.

Figure 5:
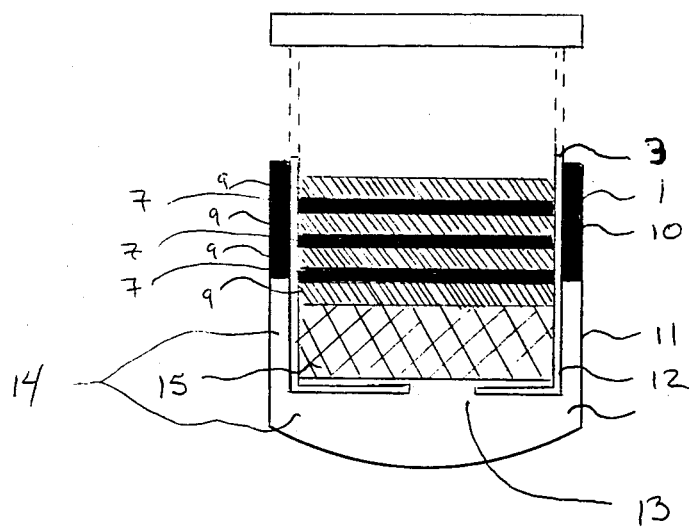

FIG. 5 is an example of a preferred embodiment of this invention which comprises a container 1 where the constant driving force is in the form of an osmotic pump which has been incorporated into the drug delivery device. The container 1 has an outer water impervious section 10, and a water permeable section 11. An inner water impermeable section 12 extends from the opening 3 to the osmotic fluid inlet 13. The outer water impermeable section 10 is optional and may be dispensed with in order to provide for a larger water permeable section 11, if desired. However, a water-tight seal must be maintained between the container 1 and the inner water impermeable section 12 at and below the opening 3 to prevent the osmotic pressure from forcing the osmotic fluid into the environment rather than against the piston 15. By varying the osmotic characteristics of the driving force, including the area provided for osmotic imbibition through the water permeable section 11, different rates at the constant driving force 2 are provided. As water passes through the permeable membrane 11 into the osmotic chamber 14 containing the osmotically active material, such as a salt, the imbibed fluid is forced through the osmotic fluid inlet 13, pushing the piston 15 and the column of drug layers 9 and spacer layers 7 towards the opening 3. By having the constant driving force part of the container itself, a very compact device is prepared.

The expansion layer is designed to rapidly expand when it is exposed to the opening and the physiological fluid within which the drug delivery device is present. Polymeric materials that expand in the presence of water such as cellulosics, for example xanthan gum, carboxymethylcellulose, methyl cellulose, alginate and the like; starches, for example amylose, amylopectin, starch derivatives such as carboxy methyl starch and the like; and synthetic polymers for example, acrylics, methacrylics and the like.

The expanding layer may be a solid tablet, a powder, paste or a film depending upon the particular expansion material used and the degree of expansion required.

The active layer, if it is separate from the expansion layer may be any convenient formulation which can be readily expelled from the drug delivery device through the opening. A liquid or paste will be convenient and readily expelled without any need for alteration prior to expulsion. The liquid or paste material should be such that it will not activate the expansion layer. However, a solid or powder formulation will also be acceptable if it is converted in the presence of the physiological fluid into a liquid or paste which can be expelled through the opening. This is conveniently accomplished since the active layer will reach the opening first giving the physiological fluid time to convert the solid or powder material into an extrudable form. When the expansion layer is activated the active layer is already prepared for extrusion out of the opening.

If the active and expansion layers are combined into a single layer as in FIGS. 3 and 5, the single layer may be a physical mixture of the expanding polymer and the medicament whereupon entrance of the physiological fluid into the layer causes rapid expansion of the entire layer forcing its explusion out of the opening. Alternatively, the combined layer may be a readily soluble or rapidly disintegrating tablet or granulation which is readily dispersed through the opening. Such a combined layer may be particularly successful with the open-ended drug delivery device shown in FIG. 4 which has a large surface area through which the combined layer may disperse. Thus, the expansion of the medicament layer may occur not only by the actual physical expansion of the layer, but also by having the expansion layer composed of a readily dispersable material such that expansion into the environment occurs as a result of the material being readily washed or eroded from the container and dispersed into the environment.

The spacer layers, also referred to as bungs, including the spacer layer closest to the constant driving force which acts as a piston, are not eroded by or expandable in the presence of the physiological or environmental fluid and are typically water impermeable elastomers such as silicone elastomers, natural or synthetic rubbers, for example polybutadiene, neoprene, nitrile, polyisoprene, SBR and the like. The spacer layers should have suitable stress-strain properties to form a water-tight but movable seal between themselves and the inner surface of the container. As aforementioned, the inner surface of the container may be lubricated or the spacer layer itself may be impregnated with a lubricant to facilitate its travel along the inner surface of the container. The spacer layer should be sufficiently firm to remain stable under the pressure of the driving force, but sufficiently flexible to maintain good contact, and thus a water-tight seal, with the inner surface of the container. Generally, material of a Shore A durometer of from 30 to 90 is suitable, preferably from 50 to 60. The spacer layer closest to the constant driving force, the piston, may be somewhat more firm than the other spacer layers.

The duration of the drug delivery pulses and the intervals between drug delivery pulses may be readily adjusted to suit any particular need by selecting the appropriate rate of expansion, dissolution or disintegration of the active and expansion layers, the rate of the constant driving force and the thickness of the spacer, active and expansion layers. It is typical to select a drug delivery pulse of from 2 hours to 4 days and an interval between pulses of from 2 to 20 days. Generally, a drug delivery pulse of from 4 hours to 1 day and an interval of from 2 to 10 days will be preferred. Depending upon the number of layers, the size of the doses and the rate of administration, a single drug delivery device of this invention can supply up to 20 doses over a period of 52 weeks.

Preferably, a pulsatile device of this invention will be designed to provide for from 5 to 15 pulses of drug over a period of from 8 to 18 weeks.

The following are examples of drug delivery systems of this invention and of their characteristics in providing for the pulsed delivery of a medicament. The examples are not to be construed as limitations of the invention.

EXAMPLE 1

The pulsatile drug delivery device consists of four 40-mg ivermectin bi-layered tablets which are contained within a modified syringe barrel. The tablets are separated from each other by uniform inert bungs. The tablets and bungs are linearly displaced by a hydraulic process driven by pressure generated from an osmotic pump.

The geometry of the unit provides for uniform pulsed delivery of the ivermectin tablets, with better than 90% of each pulse being delivered over a one-day period. The present prototype device employs a partially wax-coated 2ML4 ALZET osmotic pump (ALZA Corporation) as the drive mechanism. The wax coat was added to decrease the surface area of the permeable membrane and thus decrease the rate of drive of the osmotic pump.

EXPERIMENTAL

Tablet Compression

The composition of the bi-layered tablet granulation is reported in Table 1:

TABLE 1

| Bi-Layer Tablet Formulation | |
|---|---|
| Ingredients | Mg/Tablet |
| Active Layer | |
| Ivermectin | 44.30[1] |
| Explotab[2] | 9.00 |
| Sodium Stearate | 1.00 |
| NaCl | 20.00 |
| Disodium Edetate | 0.50 |
| Total | 74.80 |
| Swellable Layer | |
| Xanthan gum or sodium polyacrylate | 40.00 |
| Total | 114.80 |

[1]Based on 90.3% active
[2]Sodium carboxymethyl starch

All of the ingredients comprising the active layer were uniformly mixed prior to die filling. Multiple aliquots of the active (74.8 mg) and swellable polymer (40.0 mg) layer graulations were individually weighed onto glassine paper using an analytical balance. Tablet filling and compression were effected as follows:

1. The swellable polymer aliquot was added to an 8 mm stainless steel die and tapped smooth.
2. The corresponding 8 mm shallow-cup punch was used to compress lightly the filled swellable polymer layer by applying hand pressure.
3. The aliquot of active granulation was added to the die on top of the existing polymer layer.
4. Compression was accomplished using the hand-operated Carver press at a force of 0.7 metric tons for a dwell time of one minute.

Implant Fabrication

The housing of the implant device was fabricated from modified B & D (Becton-Dickinson Corp.) plastic disposable 3-ml syringes. The following modifications were made:

1. Three drug delivery ports (windows) were cut into the syringe barrel using a hand-held razor blade. The rectangular ports extended from the 20- to 26-minim calibration markings of the syringe and were 8 mm wide. Two millimeters of spacing (barrel material) remained between each window.
2. The finger grips from the top section of the syringe were removed allowing enough room for the insertion of a reversed rubber plunger bung. See step 5.
3. A rubber plunger which had been removed from the plunger stem was inserted into the syringe barrel in its normal position.
4. Bi-layered tablets and spacer bungs (see step 6) were placed into the syringe barrel on top of the plunger bung in an alternating fashion. A total of four bi-layered tablets and three spacer bungs are anticipated for the final implant.
5. Another plunger bung which had been removed from its plunger stem was inserted into the syringe barrel in a reverse position. The leading flat edge of the bung was aligned to the top edge of the drug delivery ports. This bung was secured in its position by the insertion of an extended paper clip wire through the syringe barrel just above the conical end of the reversed bung. The wire was heated in an open flame to dull red heat to facilitate this insertion process.
6. Rubber spacer bungs were prepared by several methods as follows:
    (a) Spacer bungs were cut from the flat end of the plunger bungs to a uniform thickness using a hand-held razor blade. The center holes resulting from this procedure were filled with multiple applications of Black Plastic Rubber compound, Duro Co.
    (b) Fairly circular bungs were cut from a flat rubber mat using a hand-sharpened laboratory clamp of appropriate diameter. The sharpened clamp was used in a manner similar to a cork borer.
    (c) Spacer bungs have been also cut from the conical ends of the plunger bungs. This process requires two cuts from a hand-held razor blade but results in bungs containing no center holes.
7. Eighteen-gauge, 38 mm B & D disposable needles were modified and used for physical and hydraulic connection of the implant device to the 2ML4 ALZET pumps. The length of the needles was trimmed to approximately 25 mm and the opening filed blunt.

8. The delivery rate of the ALZET 2ML4 osmotic pumps was modified by coating the outer membrane of the pumps with paraffin wax (70% Aristowax and 30% Multiwax). Coating was accomplished by dipping the blunt ends of the pumps into the molten wax. Three coats of wax were applied. The extent of coating was controlled by covering the desired amount of permeable membrane with strips of pressure sensitive tape. The equation derived relating the amount of coating achieved to the thickness of the uncoated band of pump membrane located at the delivery end of the engine is as follows: % coated=(19.8−4.4$X$) 5.05 where X equals the width of the uncoated band in centimeters.

9. The pumps were filled with water according to the instructions of the manufacturer and the modified 18-gauge needles were inserted into the pumps. Additional water was syringed into the pumps and into the small space of the implant syringe through the LEUR LOK fitting below the bottom plunger.

10. The osmotic pumps and the syringe implant housing were fitted together through the LEUR LOK fittings of the 18-gauge needle and syringe aperture.

Completeness of Dose Delivery Evaluation

To evaluate the completeness of each dose delivered from the prototype units, single bi-layered tablets-insert bung pairs were loaded into the implant housings. The tablets and bungs were advanced until the seal between the bung and housing was just broken, simulating the start of a pulsed dose. The implants were placed in distilled water maintained at 37° C. under static conditions. After one day, the amount of ivermectin delivered and that remaining within the device was determined using the spectrophotometric method discussed in this section.

Assay Methodology

The following in vitro assay methodology was used to approximate the in vivo environment of the implant:

1. The implants were allowed to deliver into 50 ml of distilled H$_2$O contained in 2×20 cm test tubes.
2. The test tubes were immersed in a water bath thermostatted at 37°±1° C.
3. At intermittent time intervals, the implants were removed from the batch and rinsed with distilled H$_2$O. The rinsed implants were placed into fresh, distilled water and returned to the bath.
4. The rinsings and the 50 ml of delivery fluid were combined and made up to 100 ml with aqueous 1.0% sodium lauryl sulfate solution.
5. One milliliter of this solution was diluted to 50 ml with distilled H$_2$O.
6. The transmittance of these solutions was measured at 245 nm in a 1-cm quartz cell using a single-beam uv-vis spectrophotometer. Distilled water was used as the reference solution.
7. The amount of ivermectin delivered was obtained by comparison to a standard curve.

RESULTS

Completeness of Dose Delivery

The results obtained for the determination of the completeness of ivermectin single-dose delivery from the prototype implant are shown in Table 2. As indicated, greater than 90% of each dose was delivered from the units within one day under static aqueous conditions at 37° C.

Delivery Profile

The delivery profiles of the accelerated prototype implant systems, similar except for their delivery rate, were evaluated in vitro. The results of these evaluations are discussed separately.

TABLE 2

Completeness of Ivermectin Delivery per Pulse[A]

| Unit No. | % Ivermectin Delivered 1st Day |
|---|---|
| 1 | 97.4 |
| 2 | 94.5 |
| 3 | 99.2 |
| 4 | 94.9 |

[A]Delivery into distilled water at 37° C. under static conditions

EXAMPLE 2

Accelerated In Vitro Study #1

In this study, a single implant device loaded with three bi-layered tablets containing magnesium stearate as the lubricant and sodium polyacrylate as the swellable polymer layer was evaluated. The spacer bungs used were those cut from a flat rubber sheet using a cork-type borer. The thickness of the spacer bungs was 1.5 mm and the tablet thickness was 2.2 mm. An unocated ALZET osmotic pump was used to drive this system with a reported delivery rate of 2.86±0.09 µl/hr.

The ivermectin delivery profile resulting from this evaluation is consistent with the osmotic pump delivery rate and known implant geometry.

Accelerated In Vitro Study #2

In this study, five implant prototype devices were simultaneously evaluated in vitro for their ivermectin pulsatile delivery characteristics. The bi-layered tablets of these implants contained sodium stearate as a lubricant and xanthan gum as the swellable polymer layer. Spacer bungs cut from the flat end of the plunger bungs were used in these devices. An initial ivermectin dose was included in these implants and hence, a total of four bi-layered tablets was loaded into the implants.

Assay of the active tablet granulation indicated a potency of 95% of the target value.

Bilayered tablet compression, implant fabrication, and drug assay were accomplished using methods identical to those used in Example 1 with the following exceptions:

1. The delivery rate of the ALZET 2ML4 osmotic pumps was modified by an 87.5% wax coating of the rate-controlling membrane. Pressure sensitive adhesive strips with an average thickness of 0.56±0.03 cm were used during the coating process.
2. The bilayered tablet formulation was used which contained xanthan gum as the swellable layer.

RESULTS

The delivery profiles obtained from five implants evaluated simultaneously are shown in Table 3 which summarizes the delivery parameters measured for each implant.

Generally, the observed single-dose delivery periods ranged from 1–3 days. The time interval between the 2nd–3rd and 3rd–4th ivermectin pulses averaged 20±2 days. This interval is consistent with the average steady-state pumping rate obtained (0.42±0.03 µl/hr)

and the geometry of the implant. Specifically, a theoretical time interval of 20.3 days is calculated from the average pumping rate (equals a linear displacement rate of 0.184 mm/day) and the average thickness of the bilayered tablets and spacer bungs (1.95 and 1.78 mm, respectively).

DISCUSSIONS AND CONCLUSIONS

The resulting delivery profiles indicate ivermectin pulses which are similar to those observed for the accelerated pulsatile implants. Hence, the single-dose delivery of ivermectin from the implant is independent of the overall osmotic pumping rate and, therefore, better than 90% of the ivermectin single doses can be expected to be delivered within 1 day.

TABLE 3

IN VITRO PULSED DELIVERY OF IVERMECTIN: 12-WEEK CATTLE IMPLANT, 87.5% WAX-COATED OSMOTIC PUMP*

| Systems | Steady-State Pump Rate $\mu l/hr$ | Time Interval Between Pulses, Days** | | | |
|---|---|---|---|---|---|
| | | 0–1 | 1–2 | 2–3 | 3–4 |
| 1 | 0.398 | 0.5 | 29 | 20 | 24.5 |
| 2 | 0.406 | 0.5 | 37 | 19.5 | 18.5 |
| 3 | 0.469 | 0.5 | 24 | 20 | 18.0 |
| 4 | 0.397 | 0.5 | 31 | 23.5 | 20 |
| 5 | 0.450 | 0.5 | 29 | 18.5 | 18 |

*Delivery into 50 ml of distilled H$_2$O at 37° C.
**Time intervals estimated at 50% pulse height.

What is claimed is:

1. A pulsatile drug delivery system which comprises an elongated container impervious to environmental fluids with an opening end and a driven end with an opening from the inside of the container to the environment at the opening end and a constant driving force operating at the driven end in a direction towards the opening end; a multiplicity of layers arranged lengthwise inside the container substantially filling the inside cross-section of the container and situated between the opening and the constant driving force with an expandable layer closest to the opening end containing one or more of a material which is therapeutically or nutritionally beneficial to be dispensed through the opening into the environment upon contact with the fluids of the environment and the layer adjacent thereto being a spacer layer inert to the fluids of the environment and the remainder of the multiplicity of layers alternating between the expandable layer and the spacer layer and wherein the rate of the dispensing of the expandable layer into the environment is greater than the rate of the constant driving force.

2. The pulsatile drug delivery system of claim 1 wherein the expandable layer is dispensed through the opening by dispersion into the fluids of the environment.

3. The pulsatile drug delivery system of claim 1 wherein the expandable layer is dispensed through the opening by expansion due to the absorption of the fluids of the environment.

4. The pulsatile drug delivery system of claim 1 wherein the expandable layer is one layer of a material which is therapeutically or nutritionally beneficial and a separate layer of a material expandable upon contact with the environment wherein the drug containing material is dispensed through the opening by the force exerted by the expandable layer upon the layer containing the therapeutically or nutritionally beneficial material.

5. The pulsatile drug delivery system of claim 1 wherein the layers are of varying sizes materials and dispensing characteristics such that a non-uniform series of pulses is provided.

6. The pulsatile drug delivery system of claim 1 wherein the expandable layer contains a polymeric material which expands upon contact with the fluids of the environment.

7. The pulsatile drug delivery system of claim 6 wherein the polymeric material is xanthan gum, carboxymethylcellulose, methyl cellulose, alginate, amylose, amylopectin, carboxymethyl starch, acrylics or methyacrylics.

8. The pulsatile drug delivery system of claim 1 wherein the constant driving force is provided by an osmotic pump.

9. The pulsatile drug delivery system of claim 8 wherein the osmotic pump is incorporated within the container of the pulsatile drug delivery system.

10. The pulsatile drug delivery system of claim 1 wherein the opening end of the container is provided with a storage area for the spacer layers.

11. The pulsatile drug delivery system of claim 10 wherein the opening is a circumferential series of spaces through the container.

12. The pulsatile drug delivery system of claim 1 wherein the opening comprises the entire cross-section of the container.

13. The pulsatile drug delivery system of claim 1 which is for oral administration.

14. The pulsatile drug delivery system of claim 13 which is for oral administration to ruminant animals.

15. The pulsatile drug delivery system of claim 14 which is provided with densifying agents or variable geometry to cause the retention of the system in the rumen.

16. The pulsatile drug delivery system of claim 1 which is parenterally implanted.

17. The pulsatile drug delivery system of claim 16 wherein the parenteral implant is subcutaneous.

18. The pulsatile drug delivery system of claim 1 wherein the drug being administered is a therapeutic agent.

19. The pulsatile drug delivery system of claim 18 wherein the therapeutic agent is ivermectin.

20. The pulsatile drug delivery system of claim 1 wherein the drug being administered is a supplemental nutrient material.

* * * * *